US008940246B2

(12) United States Patent
Neel et al.

(10) Patent No.: US 8,940,246 B2
(45) Date of Patent: Jan. 27, 2015

(54) METHOD AND APPARATUS FOR CODING DIAGNOSTIC METERS

(75) Inventors: Gary T. Neel, Weston, FL (US); Brent E. Modzelewski, Boca Raton, FL (US); George R. Rounds, Coconut Creek, FL (US); Carlos Oti, Plantation, FL (US); Allan Javier Caban, Lake Worth, FL (US); Jeffrey Akins, Boca Raton, FL (US)

(73) Assignee: Nipro Diagnostics, Inc., Fort Lauderdale, FL (US)

( * ) Notice: Subject to any disclaimer, the term of this patent is extended or adjusted under 35 U.S.C. 154(b) by 902 days.

(21) Appl. No.: 11/934,004

(22) Filed: Nov. 1, 2007

(65) Prior Publication Data

US 2008/0134810 A1  Jun. 12, 2008

Related U.S. Application Data

(63) Continuation-in-part of application No. 11/373,284, filed on Mar. 13, 2006.

(51) Int. Cl.
*G01N 21/75* (2006.01)
*G01N 31/22* (2006.01)
*G01N 33/487* (2006.01)
(Continued)

(52) U.S. Cl.
CPC .......... *G01N 33/48757* (2013.01); *B01L 3/545* (2013.01); *G01N 33/48771* (2013.01); *A61B 10/0096* (2013.01); *A61B 2017/00482* (2013.01); *B01L 2300/027* (2013.01); *B01L 2300/041* (2013.01); *B01L 2300/046* (2013.01); *B01L 2300/0825* (2013.01)
USPC ........... 422/402; 422/400; 422/401; 422/403; 422/404; 422/408; 422/430; 436/164; 436/165; 436/169; 435/287.7; 73/866

(58) Field of Classification Search
None
See application file for complete search history.

(56) References Cited

U.S. PATENT DOCUMENTS 3,582,335 A  6/1971  Erlichman
3,918,910 A  11/1975  Soya et al.
(Continued)

FOREIGN PATENT DOCUMENTS

DE  10 2004 062 255 B3  2/2006
EP     0 059 350 A1  9/1982
(Continued)

OTHER PUBLICATIONS

Office Action mailed Apr. 29, 2009, in co-pending U.S. Appl. No. 11/930,862 (12 pages).
(Continued)

*Primary Examiner* — Neil N Turk
(74) *Attorney, Agent, or Firm* — Greenberg Traurig, LLP; Roman Fayerberg; David J. Dykeman

(57) ABSTRACT

A system for diagnostic testing may include a meter for performing a diagnostic test on a sample applied to a test media, the meter having a housing and an interface for receiving a signal representing coding information, and a container configured to contain test media compatible with the meter, the container having a coding element associated therewith. Additionally, the system may provide a mechanism for removing the meter from an interconnected test container and reattaching it to a new container using on-container coding methods that can recalibrate the meter for the new container of test strips.

13 Claims, 11 Drawing Sheets

(51) Int. Cl.
*B01L 3/00* (2006.01)
*G01N 33/52* (2006.01)
*G01N 21/77* (2006.01)
*G01N 33/00* (2006.01)
*A61B 10/00* (2006.01)
*A61B 17/00* (2006.01)

(56) References Cited

U.S. PATENT DOCUMENTS

| | | | |
|---|---|---|---|
| 4,064,760 A * | 12/1977 | Benjamin | 73/863.52 |
| 4,100,559 A | 7/1978 | Wareham et al. | |
| 4,142,863 A | 3/1979 | Covington et al. | |
| 4,162,736 A * | 7/1979 | Faulstich | 215/256 |
| 4,279,861 A | 7/1981 | Jessop | |
| 4,834,234 A | 5/1989 | Sacherer et al. | |
| 4,911,344 A | 3/1990 | Kahler | |
| 5,102,624 A | 4/1992 | Muraishi | |
| 5,119,830 A * | 6/1992 | Davis | 600/584 |
| 5,154,889 A | 10/1992 | Muraishi | |
| 5,244,116 A | 9/1993 | Leo | |
| 5,281,395 A | 1/1994 | Markart et al. | |
| 5,298,425 A | 3/1994 | Kuhn et al. | |
| 5,489,414 A | 2/1996 | Schreiber et al. | |
| 5,505,308 A | 4/1996 | Eikmeier et al. | |
| 5,510,266 A | 4/1996 | Bonner et al. | |
| 5,575,403 A | 11/1996 | Charlton et al. | |
| 5,609,823 A | 3/1997 | Harttig et al. | |
| 5,630,986 A | 5/1997 | Charlton et al. | |
| 5,660,791 A | 8/1997 | Brenneman et al. | |
| 5,679,311 A | 10/1997 | Harttig et al. | |
| 5,700,695 A | 12/1997 | Yassinzadeh et al. | |
| 5,714,123 A | 2/1998 | Sohrab | |
| 5,720,924 A | 2/1998 | Eikmeier et al. | |
| 5,797,693 A | 8/1998 | Jaeger | |
| 5,810,199 A | 9/1998 | Charlton et al. | |
| 5,854,074 A | 12/1998 | Charlton et al. | |
| 5,856,195 A | 1/1999 | Charlton et al. | |
| 5,863,800 A | 1/1999 | Eikmeier et al. | |
| 5,872,713 A | 2/1999 | Douglas et al. | |
| 5,989,197 A | 11/1999 | Avaltroni | |
| 5,989,917 A | 11/1999 | McAleer et al. | |
| 6,106,780 A | 8/2000 | Douglas et al. | |
| 6,168,957 B1 | 1/2001 | Matzinger et al. | |
| 6,176,119 B1 | 1/2001 | Kintzig | |
| 6,283,982 B1 | 9/2001 | Levaughn et al. | |
| 6,377,894 B1 | 4/2002 | Deweese et al. | |
| 6,398,067 B1 | 6/2002 | Belfance et al. | |
| 6,428,664 B1 | 8/2002 | Bhullar et al. | |
| 6,472,220 B1 | 10/2002 | Simons et al. | |
| 6,488,828 B1 | 12/2002 | Bhullar et al. | |
| 6,508,380 B1 | 1/2003 | von Schuckmann | |
| 6,534,017 B1 | 3/2003 | Bottwein et al. | |
| 6,544,475 B1 | 4/2003 | Douglas et al. | |
| 6,558,528 B1 | 5/2003 | Matzinger | |
| 6,682,704 B2 | 1/2004 | Bottwein et al. | |
| 7,063,234 B2 | 6/2006 | Giraud | |
| 7,070,053 B1 | 7/2006 | Abrams et al. | |
| 7,138,089 B2 | 11/2006 | Aitken et al. | |
| 7,213,720 B2 | 5/2007 | Giraud | |
| 7,276,027 B2 | 10/2007 | Haar et al. | |
| 2002/0057993 A1 | 5/2002 | Maisey et al. | |
| 2002/0076349 A1 | 6/2002 | Aitken et al. | |
| 2002/0081233 A1* | 6/2002 | Lappe et al. | 422/82.05 |
| 2002/0104849 A1 | 8/2002 | Giruad | |
| 2002/0188224 A1 | 12/2002 | Roe et al. | |
| 2003/0031591 A1 | 2/2003 | Whitson et al. | |
| 2003/0031595 A1 | 2/2003 | Kirchhevel et al. | |
| 2003/0032190 A1 | 2/2003 | Brown et al. | |
| 2003/0036200 A1 | 2/2003 | Charlton | |
| 2003/0047451 A1 | 3/2003 | Bhullar et al. | |
| 2003/0059350 A1 | 3/2003 | Sacherer | |
| 2003/0089730 A1 | 5/2003 | May et al. | |
| 2003/0116583 A1 | 6/2003 | Pugh | |
| 2003/0129346 A1 | 7/2003 | Pearson et al. | |
| 2003/0133847 A1 | 7/2003 | Hagen et al. | |
| 2003/0175155 A1 | 9/2003 | Charlton | |
| 2003/0178437 A1 | 9/2003 | Crawford | |
| 2003/0185705 A1 | 10/2003 | Otake | |
| 2003/0185708 A1 | 10/2003 | Otake | |
| 2003/0186446 A1 | 10/2003 | Pugh | |
| 2003/0191415 A1 | 10/2003 | Moerman et al. | |
| 2003/0203498 A1 | 10/2003 | Neel et al. | |
| 2003/0211619 A1 | 11/2003 | Olson et al. | |
| 2003/0212344 A1 | 11/2003 | Yuzhakov et al. | |
| 2003/0212345 A1 | 11/2003 | McAllister et al. | |
| 2003/0219357 A1 | 11/2003 | Douglas et al. | |
| 2003/0223906 A1 | 12/2003 | McAllister et al. | |
| 2004/0007585 A1 | 1/2004 | Griffith et al. | |
| 2004/0038411 A1 | 2/2004 | Hayter et al. | |
| 2004/0048394 A1 | 3/2004 | Kirchhevel | |
| 2004/0057878 A1 | 3/2004 | House et al. | |
| 2004/0178216 A1 | 9/2004 | Brickwood et al. | |
| 2005/0019953 A1 | 1/2005 | Groll | |
| 2005/0023137 A1 | 2/2005 | Bhullar et al. | |
| 2005/0143675 A1 | 6/2005 | Neel et al. | |
| 2006/0094986 A1 | 5/2006 | Neel et al. | |
| 2006/0189895 A1 | 8/2006 | Neel et al. | |
| 2006/0275890 A1 | 12/2006 | Neel et al. | |
| 2007/0212258 A1 | 9/2007 | Neel et al. | |
| 2008/0118400 A1 | 5/2008 | Neel et al. | |

FOREIGN PATENT DOCUMENTS

| | | |
|---|---|---|
| EP | 0 064 691 A1 | 11/1982 |
| EP | 0 064 691 B1 | 3/1986 |
| EP | 0 255 675 B1 | 5/1992 |
| EP | 0 732 590 A2 | 9/1996 |
| EP | 0 732 590 A3 | 5/1997 |
| EP | 0 779 226 A1 | 6/1997 |
| EP | 0 622 119 B1 | 11/1999 |
| EP | 1 022 565 A2 | 7/2000 |
| EP | 1 225 448 A2 | 7/2002 |
| EP | 1 285 695 A2 | 2/2003 |
| EP | 1 286 162 A2 | 2/2003 |
| EP | 1 329 395 A1 | 7/2003 |
| EP | 1 362 801 A2 | 11/2003 |
| EP | 1 369 083 A1 | 12/2003 |
| EP | 1 806 588 A1 | 7/2007 |
| WO | WO 94/10558 | 5/1994 |
| WO | WO 94/29703 A1 | 12/1994 |
| WO | WO 97/29847 A1 | 8/1997 |
| WO | WO 01/23885 A1 | 4/2001 |
| WO | WO 02/08753 A2 | 1/2002 |
| WO | WO 02/055008 A2 | 7/2002 |
| WO | WO 02/078533 A2 | 10/2002 |
| WO | WO 03/042691 A1 | 5/2003 |
| WO | WO 03/082091 A2 | 10/2003 |
| WO | WO 03/082092 A1 | 10/2003 |
| WO | WO 03/083469 A2 | 10/2003 |
| WO | WO 2004/011068 A1 | 2/2004 |
| WO | WO 2004/041082 A1 | 5/2004 |
| WO | WO 2004/041672 A2 | 5/2004 |
| WO | WO 2004/044142 A2 | 5/2004 |
| WO | WO 2004/070381 | 8/2004 |
| WO | WO 2005/040793 A1 | 5/2005 |
| WO | WO 2006/076721 A2 | 7/2006 |
| WO | WO 2007/050396 A1 | 5/2007 |
| WO | WO 2007/085438 A2 | 8/2007 |
| WO | WO 2007/090662 A1 | 8/2007 |
| WO | WO 2007/108900 A1 | 9/2007 |
| WO | WO 2008/063405 A1 | 5/2008 |

OTHER PUBLICATIONS

Office Action mailed Jun. 9, 2009, in co-pending U.S. Appl. No. 11/373,284 (20 pages).
International Search Report and Written Opinion for PCT/US2008/081691, mailed Jan. 29, 2009.
XP-002397571, "ACCU-CHEK® Compact Plus User's Manual," Roche Diagnostics GmbH, Jan. 2005.
Office Action mailed Jul. 20, 2010, in co-pending U.S. Appl. No. 11/373,284, filed Mar. 13, 2006.

(56) References Cited

OTHER PUBLICATIONS

Office Action mailed Feb. 12, 2010, in co-pending U.S. Appl. No. 11/373,284, filed Mar. 13, 2006.
Office Action mailed Mar. 15, 2010, in co-pending U.S. Appl. No. 11/930,862, filed Oct. 31, 2007.
Office Action mailed Nov. 25, 2009, in co-pending U.S. Appl. No. 11/930,862, filed Oct. 31, 2007.
International Search Report mailed Oct. 8, 2009 from the European Patent Office in Application No. PCT/US2008/081432.

* cited by examiner

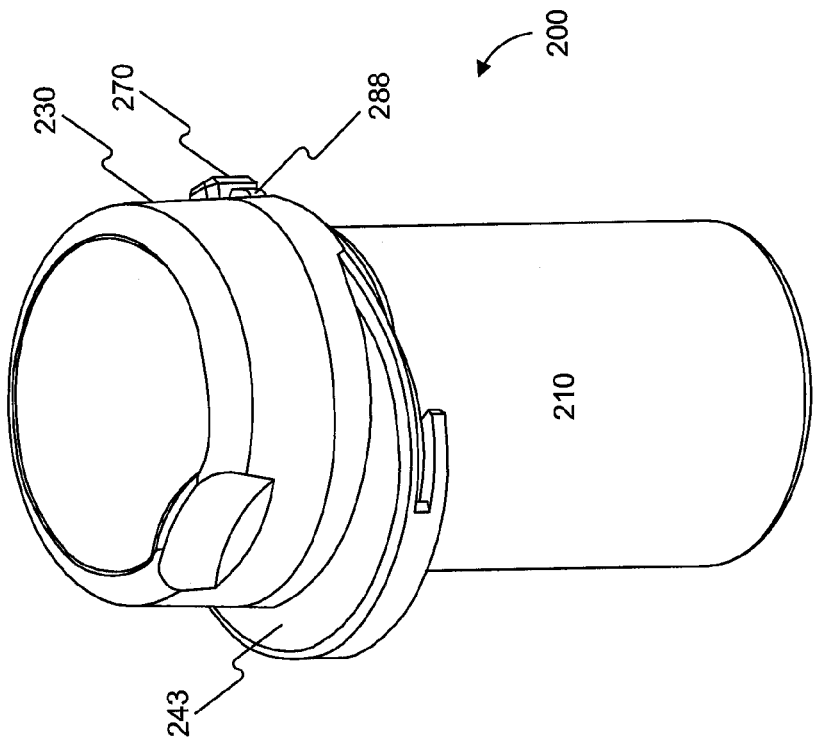
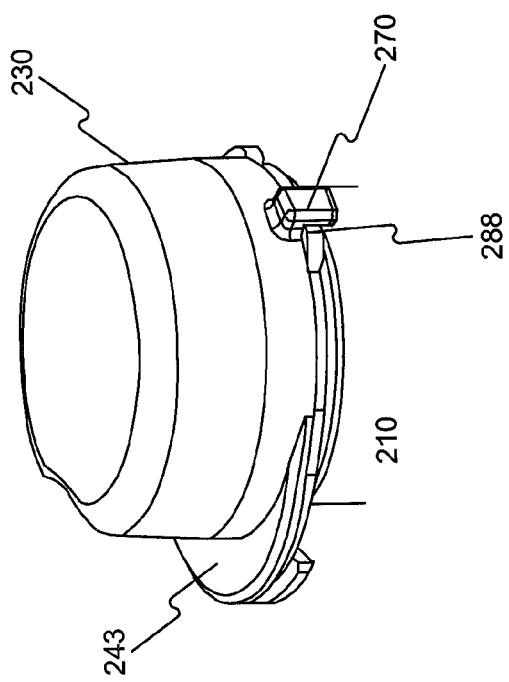
FIG. 1A
FIG. 1B

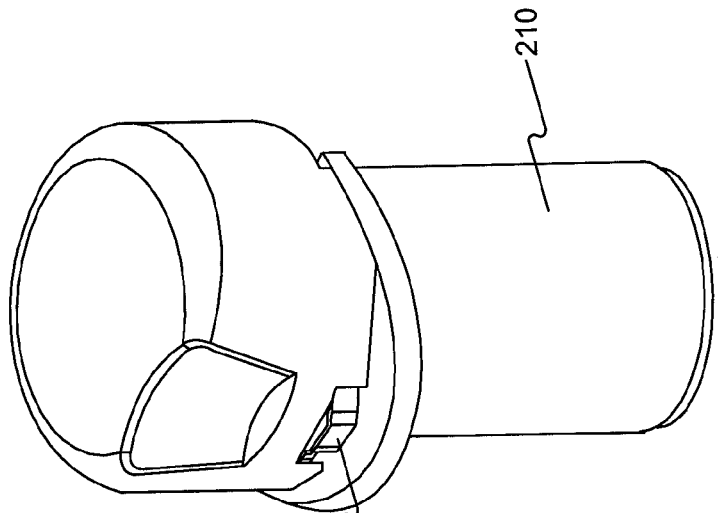
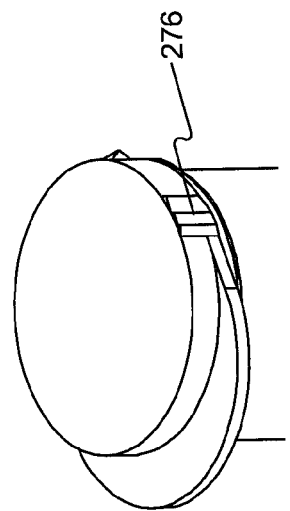
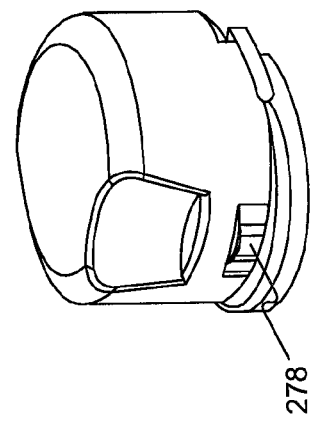

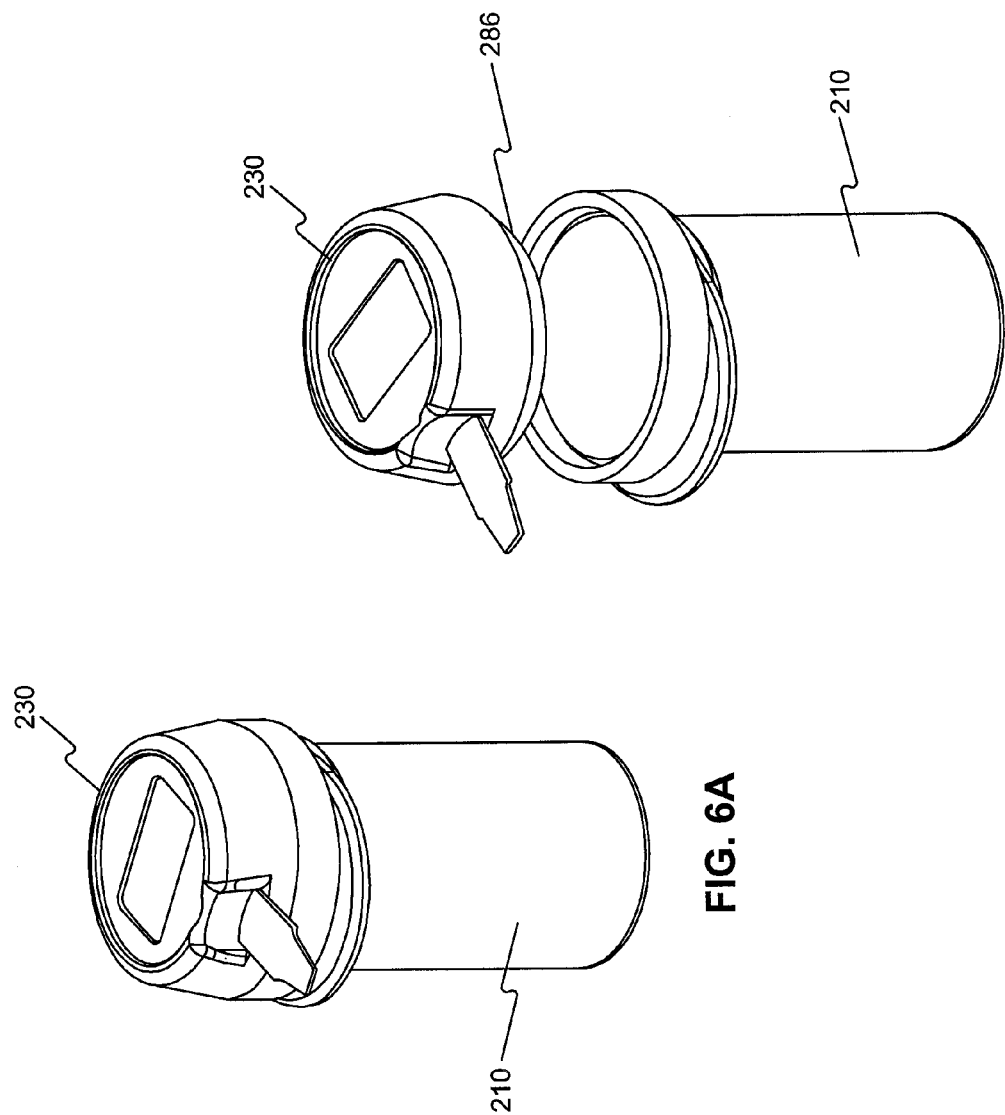

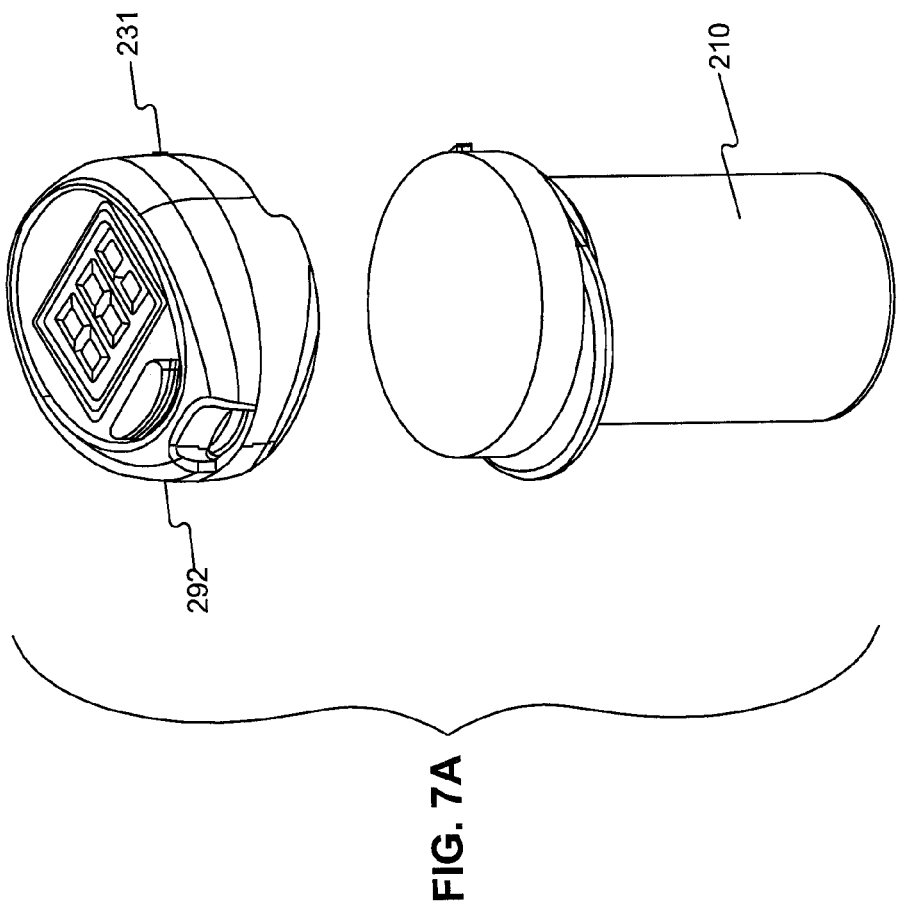

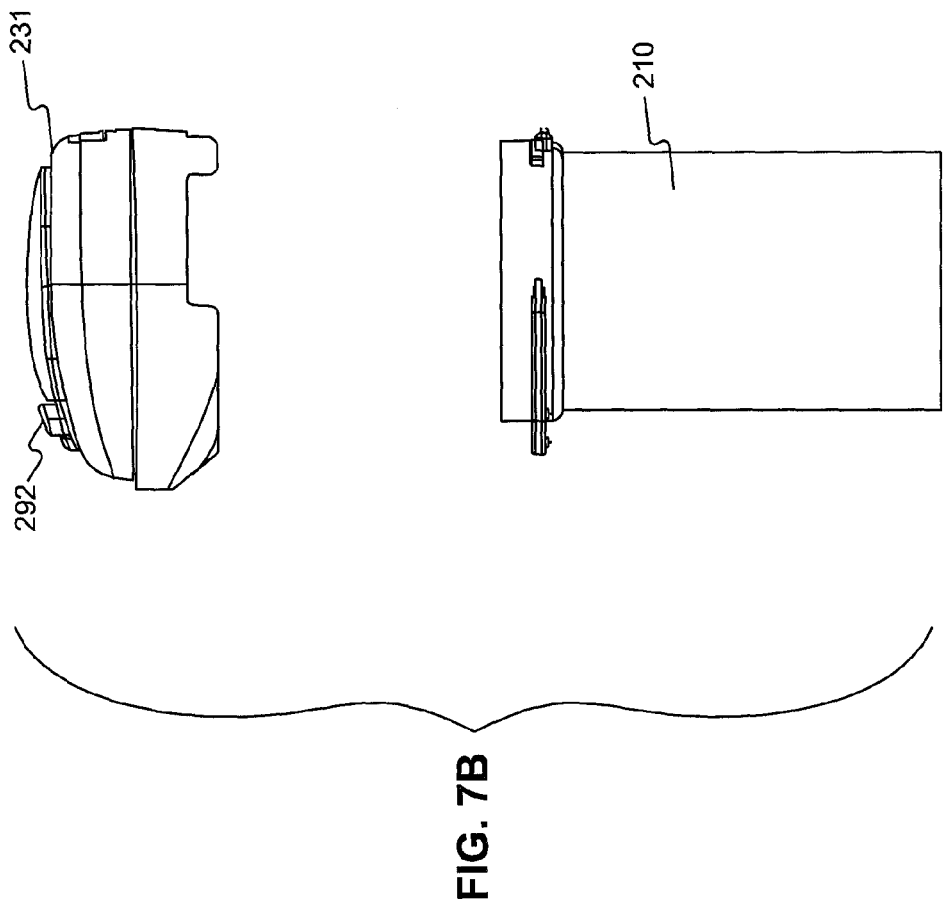

METHOD AND APPARATUS FOR CODING DIAGNOSTIC METERS

CROSS-REFERENCE TO RELATED APPLICATIONS

This application is a continuation-in-part of U.S. Ser. No. 11/373,284, filed Mar. 13, 2006, which is herein incorporated by reference in its entirety.

TECHNICAL FIELD

The present invention relates to the field of diagnostic testing and, more particularly, to diagnostic testing systems using electronic meters.

BACKGROUND

Diagnostic testing systems are commonly used to perform various types of diagnostic tests on various types of samples. The diagnostic test may be a qualitative or quantitative test to determine the presence, concentration or amount of one or more analytes in a sample. The analyte may be a medically significant analyte—e.g., glucose, ketones, cholesterol, triglycerides, human choriogonadotropin (HCG), hemoglobin A1C, fructosamine, carbohydrates, tumor markers, lead, anti-epilepsy drugs, bilirubin, liver function markers, toxins or their metabolites, controlled substances, blood coagulation factors (PT, ATPP), etc.—contained in a biological sample—e.g., blood, urine, tissue, saliva, etc. But the diagnostic test is not limited to the medical field. In addition, diagnostic test meters can be used to monitor analytes or chemical parameters in non-medical samples such as water, soil, sewage, sand, air, or any other suitable sample.

Such diagnostic testing systems may include a test media (e.g., a test strip, tab, disc, etc.) configured to react to the presence of the analyte in a sample, and a separate electronic meter configured to interface with the test media in order to conduct the diagnostic test and indicate the results of the diagnostic test to the user.

In order to conduct the diagnostic test, a user must first obtain a sample test media, e.g., a test strip, from a container, then obtain a sample using a sampling device (e.g., by drawing blood using a lancet), and then apply the sample to the test media (either before or after inserting the test media into the meter interface). The meter then performs the diagnostic test on the sample and indicates the result to the user, e.g., using a numerical display.

Prior art diagnostic meters are sometimes bulky because the housings contain the display, electronics, and test media. In addition, the user of a blood testing diagnostic system must manage and carry not only the meter, but also a test media container and a sampling device. These three components must be manipulated in a certain order, which requires a substantial amount of attention and manipulation to conduct a successful test. Not only are the steps cumbersome to some users, there exists the possibility that the test media container, sampling device, and meter could be separated from each other, so that the user may find themselves without one or more of the components necessary to conduct the diagnostic test.

As is known in the art, test media from different manufacturers or media from different manufacturing lots may respond differently to the presence or concentration of analyte in the sample. In order to obtain more accurate results, the electronic meter may be calibrated with respect to a given test strip from a brand or lot of test strips by providing it with one or more brand- or lot-specific calibration parameters that correlate the signal response from a particular brand or lot of test media to a standardized reference. By such calibration, the results reported by the meter more accurately represent the amount of analyte in a sample.

Before running a diagnostic test, the meter needs to be properly calibrated. The user may be required to provide the meter with the appropriate calibration parameters in a separate "coding" step. For example, the test media container may bear a code number which is entered into the meter, and from which the meter can access the appropriate calibration information stored in the meter's memory. The code number can be entered manually (e.g., using buttons or other user input devices on the meter) so as to provide the calibration data to the meter. Alternatively, the calibration data may be downloaded, e.g., from a manufacturer's website. In another approach, the test media container may be provided with an associated code chip, e.g. a ROM, in which the calibration data is stored electronically. The user may provide the calibration data to the meter by inserting the code chip into a corresponding port on the meter.

These prior art coding methods can be inconvenient or difficult for the user. For example, elderly or infirm users may have difficulty downloading calibration data or inserting code chips, which must be physically aligned properly in order to achieve a data connection with the meter. Code chips can be misplaced or lost, leading to the inability to use corresponding test media, or using the test media with an unmatched coding device. Further, users may forget to calibrate the meter for use with a new brand or lot of test media. Consequently, the user may enter incorrect calibration parameters or codes, or the user may use test media from one brand or lot with a meter calibrated for use with test media from a different brand or lot. Once a meter is calibrated for a given lot of test media, the use of that meter with test media from another lot may lead to erroneous results that could have serious consequences for the user. For instance, where the test is a self-test of blood glucose level, an erroneous result could lead the user to act, or fail to act, in a manner detrimental to his or her health.

A possible solution to the above-mentioned coding problems is to insure that all marketed media behave the same. This approach is referred to as "universal coding." Universal coding schemes use strip lots that are controlled and sorted to a narrow acceptance criteria, i.e., all strips are conformed to a single set of calibration parameters, thus eliminating the needs for multiple sets of parameters to be stored in the meter. Universal coding saves the cost of replacing the meter by allowing it to be used with many different test strip containers. From a manufacturing perspective, universally coded media needs to be tightly controlled such that manufactured strip lots have the same behavior, and hence code, in order to fit the meter's fixed calibration data. This method is not technique dependent and helps prevent errors due to mixed strip lots. Furthermore, universal coding always has the correct code such that there is no miss-match between the meter and the strip lot code. However, the narrow limits imposed by this method do not conform well to large-scale manufacturing processes, which include inherent variances. It is nearly impossible using high-throughput, batch-oriented manufacturing techniques to ensure that test media will exhibit perfectly consistent behavior; thus, the universal coding scheme invariably results in non-conforming lots of media. This media will be unusable, adding to cost and undesirable waste.

Accordingly, there is a need for diagnostic testing systems that are convenient to carry and that minimize the chance that a user will use a diagnostic meter with test media from a brand or lot for which the meter has not been calibrated.

A need also remains for removable meters than can be removed from one test container and reused with a different test container.

SUMMARY

The illustrative embodiments described herein meet these and other needs by providing a diagnostic testing system including a meter for performing a diagnostic test on a sample applied to a test media, the meter having a housing and an interface for receiving a signal representing coding information, and a container configured to contain test media compatible with the meter, the container having a coding element associated therewith, wherein transferring the meter from an associated test container to a new container includes using one of several coding methods that transfer lot specific code information from the new container of media to the meter.

Also provided herein further provide a meter housing with a receptacle that can receive a test strip container. Additionally, the meter housing may be configured to receive devices such as at least one of media players, terrestrial or satellite radios, travel alarm clocks, test alarms, memo voice recorders, PDAs, cell phones, or other add-on functionality, such that a code, similar to one placed on the test strip container, can be read in order for the device to be used in conjunction with the meter.

Disclosed herein is a meter housing capable of being removed from a first container and attached to a second container. The meter housing may be configured with at least one top mount attachment configured to releasably engage the meter housing and the container.

In an embodiment, the meter housing is configured to be removed by rotating the meter housing a sufficient distance to disengage the meter housing from the container. For example, the meter housing may be rotated at least about an ⅛ of a revolution, at least about an ¼ of a revolution, or at least about an ½ of a revolution.

In another embodiment, the container is configured to be removed by rotating the container a sufficient distance to disengage the container from the meter housing. For example, the container may be rotated at least about an ⅛ of a revolution, at least about an ¼ of a revolution, or at least about an ½ of a revolution.

In yet another embodiment, the top mount attachment is a hook capable of releasing the meter housing from the container. In another embodiment, the top mount attachment is a ring. In another embodiment, the meter housing comprises a press fit post and the container comprises an orifice configured to receive the press fit post. In an embodiment, the top mount attachment is a combination of a lock and a protrusion. In an embodiment, the top mount attachment is a tab.

Additional aspects and advantages of the invention will be set forth in part in the description which follows, and in part will be obvious from the description, or may be learned by practice of the invention. The advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description, serve to explain the principles of the invention.

FIG. 1A is a perspective view of an integrated system consistent with the embodiments disclosed herein.

FIG. 1B is another view of the integrated system depicted in FIG. 1A.

FIG. 4A is a perspective view of an integrated system consistent with the embodiments disclosed herein.

FIG. 4B is another view of the integrated system depicted in FIG. 4A.

FIG. 4C is another view of the integrated system depicted in FIG. 4A.

FIG. 6A is a perspective view of an integrated system consistent with the embodiments disclosed herein.

FIG. 6B is another view of the integrated system depicted in FIG. 6A.

FIG. 7A is a view of a embodiment of an integrated system including a meter housing capable of being released from a container by depressing an eject button.

FIG. 7B is another view of the integrated system depicted in FIG. 7B.

DESCRIPTION OF THE EMBODIMENTS

Reference will now be made in detail to the exemplary embodiments of the invention, examples of which are illustrated in the accompanying drawings. Wherever possible, the same reference numbers will be used throughout the drawings to refer to the same or like parts.

Figure 9:
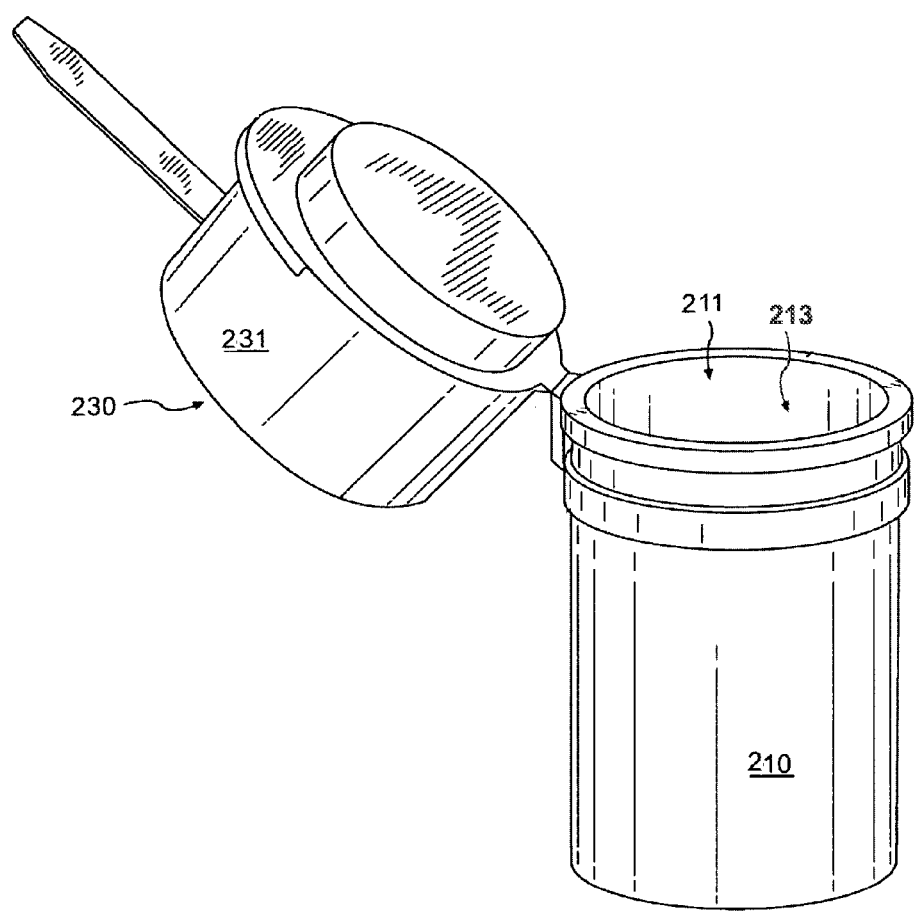
FIG. 9 is a perspective view of an embodiment of an integrated system consistent with the embodiments disclosed herein.

FIGS. 1A and 1B depict an integrated system 200 for conducting a diagnostic test in accordance with an exemplary embodiment of the present invention. Exemplary integrated system 200 includes a container 210 for containing test media, such as test strips, and a meter 230 for performing a diagnostic test using the test strips contained in container 210. The plurality of test strips may be contained in an interior volume 213 of container 210. Such an interior volume may be open, as shown in FIG. 9, permitting contact between test strips contained therein.

Meter 230 may be contained within a meter housing 231. Meter housing 231 is attached to or otherwise includes a top mount attachment 270 that engages container 210 in order to selectively close an opening 211 of the container. As would be apparent to one of ordinary skill in the art, and as discussed herein, attached may be used to signify affiliated with, associated with, affixed with/to, connected with/to, coupled with/to, fastened with/to, fixed with/to, secured with/to, etc.

In the embodiment depicted in FIGS. 1A and 1B, top mount attachment 270 is a lock. Lock 270 extends from meter housing 231 and is configured to engage a corresponding protrusion 288 on container 210. Protrusion 288 may be located along a portion of the upper lip of container 210.

In yet another embodiment, meter housing 231 comprises a tab 272 positioned along the side wall of housing 231. Tab 272 extends beyond the side wall to facilitate the user in removing housing 231 from container 210, for example, by pushing upward, for example, with a finger or thumb against tab 272.

In one embodiment, tab 272 comprises one or more ridges to aid the user in applying force to tab 272. The ridges may function to prevent the user's finger or thumb from slipping from tab 272.

In another embodiment, tab 272 may extend at an angle away from the side wall of housing 231. When measured relative to a vertical plane parallel to the side wall of housing 231, the angle of tab 272 ranges from about 1 degrees to about 90 degrees, from about 20 degrees to about 70 degrees, or from about 40 degrees to about 50 degrees. The angle may measure about 45 degrees.

Figure 2A:
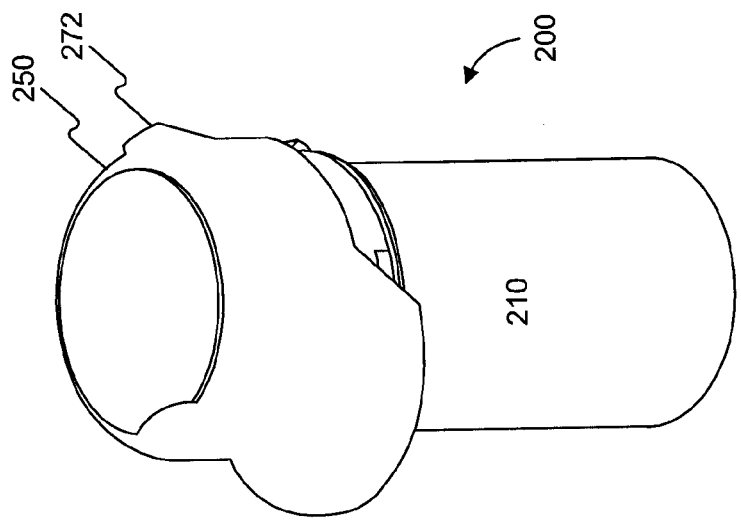
FIG. 2A is a perspective view of an integrated system consistent with the embodiments disclosed herein.
Figure 2B:
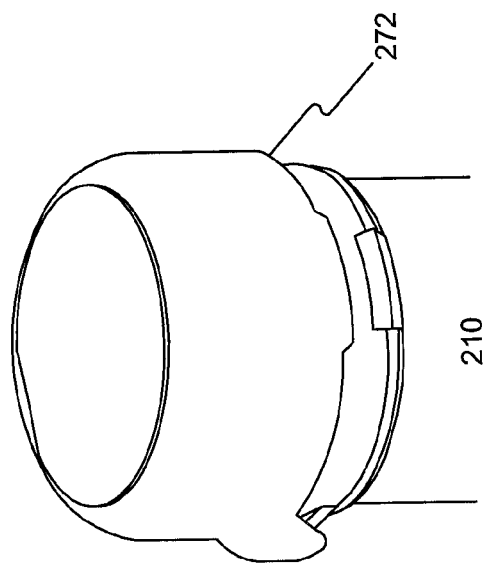
FIG. 2B is another view of the integrated system depicted in FIG. 2B.

Although FIGS. 2A and 2B depict a single protrusion, the skilled artisan readily understands that the top mount attachment may comprise more than one tab. For example, two tabs may be spaced apart up to about 180 degrees from one another, and the user may hold container 210 push upward on each tab while anchoring the container, for example, in the palms of both hands or on a surface.

Figure 3A:
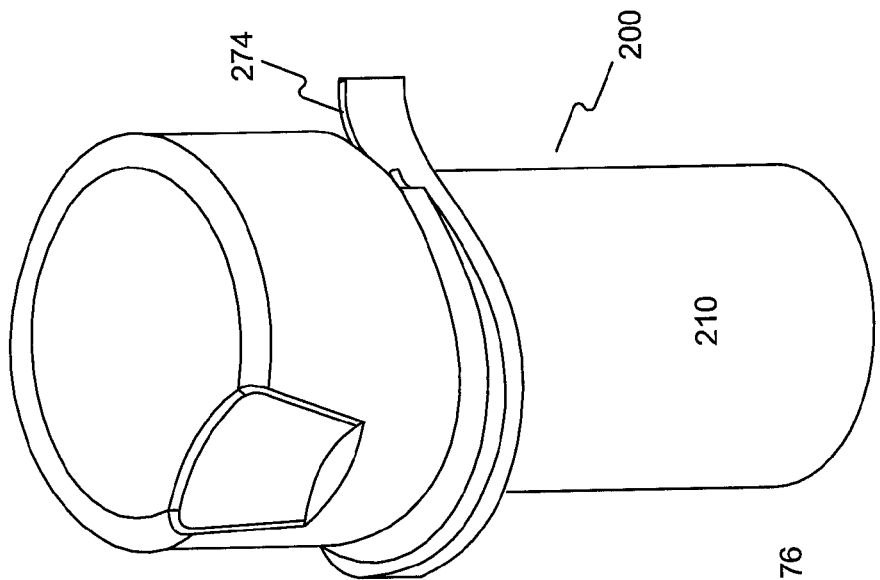
FIG. 3A is a perspective view of an integrated system consistent with the embodiments disclosed herein.
Figure 3C:
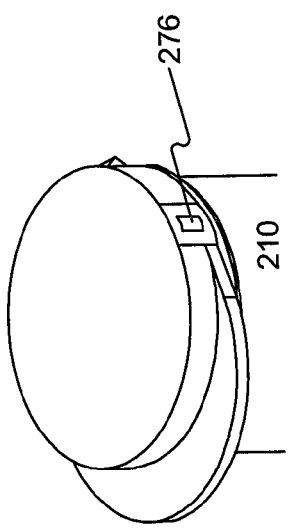
FIG. 3C is another view of the integrated system depicted in FIG. 3A.
Figure 3B:
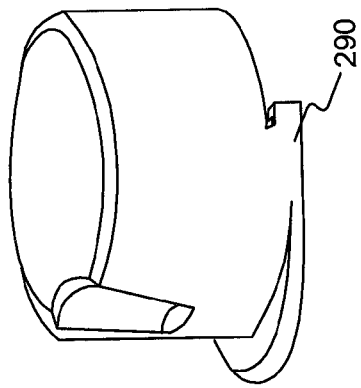
FIG. 3B is another view of the integrated system depicted in FIG. 3A.

FIGS. 3A, 3B, and 3C depict yet another top mount attachment for releasably attaching meter housing 231 to container 210. In this embodiment, meter housing 231 comprises at least one lever 274 and at least one hook 290 interconnected so that applying a force to at least one lever 274 moves at least one hook 290. Lever 274 comprises a flexible material and/or flexible configuration. Container 210 comprises at least one detent 276 capable of receiving hook 290. A user removes housing 231 by squeezing lever 274 towards housing 231. Squeezing lever 274 in the direction towards housing 231 releases hook 290 from detent 276. Housing 231 may then be removed from the top end of container 210.

FIGS. 3A-3C depict one lever, one hook, and one detent configured to work together as a single closure mechanism. The skilled artisan readily understands that more than one combination of lever, hook, and detent may be used. In an exemplary embodiment, the top mount attachment comprises two levers, two hooks, and two corresponding detents.

In a further embodiment, the meter housing comprises a mechanism, for example, a button, configured to actuate the at least one hook. FIGS. 4A, 4B, and 4C comprise yet another configuration for top mount attachment comprising at least one lever 274, at least one detent 276, and a button 278. Button 278 and at least one detent 276 are interconnected so that pressing button 278 engages detent 276. When detent 276 is positioned within a recessed area (not shown) of container 210, pressing button 278 releases detent 276 from the recessed area. To attach housing 231 to container 210, a user may position housing 231 adjacent to container 210 so that detent 276 and the recessed area are aligned. Pressing button 278 allows detent 276 to engage the recessed area.

In a further embodiment, button 278 is configured to disengage detent 276 from meter housing 231. In this embodiment, the step of pressing button 278 allows the meter housing 231 to be removed from container 210. To reattach meter housing 231 to container 210 or to a second container, the user may snap meter housing 231 onto container 210 or a second container.

Button 278 may be comfortably pressed with the right thumb or index finger while the integrated system 200 is held in the right hand. But button 278 may be positioned elsewhere on meter housing 231. For example, button 278 may be placed on a right hand side of meter housing 231 in order to be more convenient for left handed users or on a top portion of the meter 230.

Figure 5A:
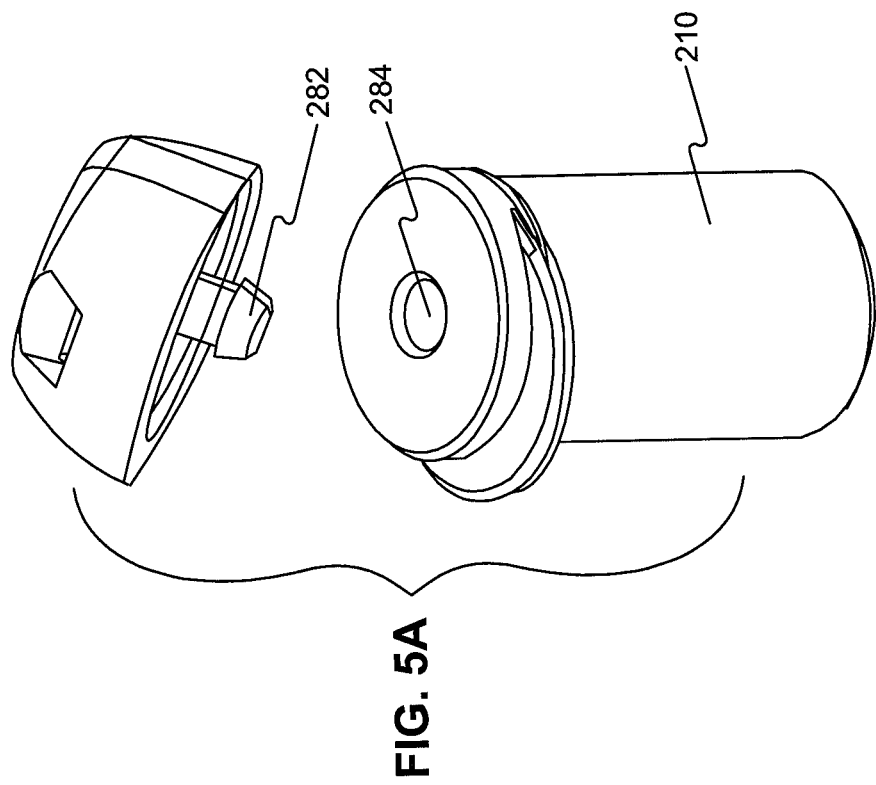
FIG. 5A is a perspective view of an integrated system consistent with the embodiments disclosed herein.
Figure 5B:
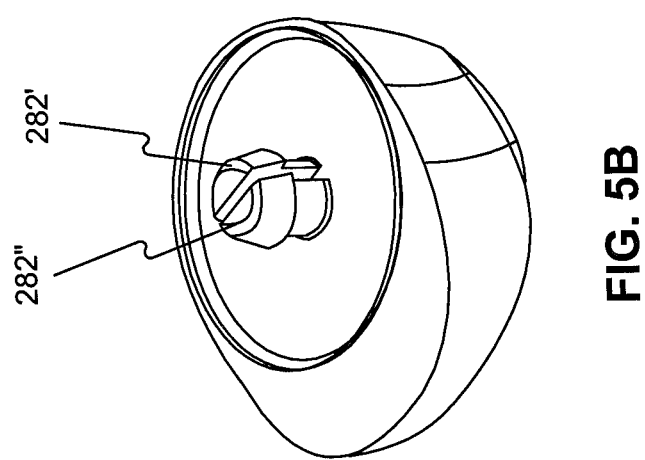
FIG. 5B is another view of the integrated system depicted in FIG. 5A.

FIGS. 5A and 5B depict a top mount attachment comprising a press fit post 282. Container 231 comprises press fit post 282 and container 210 comprises an orifice 284 sized to receive press fit post 282. Press fit post 282 fits within orifice 284, thereby sealing orifice 284 against the infiltration of light, liquid, and vapor. In an embodiment depicted in FIG. 5B, press fit post 282 comprises partial post 282' and partial post 282". Partial post 282' and partial post 282" are spaced apart creating a hollow strip.

In yet another embodiment, a connector attaches container 210 to housing 231. The connector may be releasably attached to container 210 and/or housing 231. In the embodiment depicted in FIGS. 6A and 6B, the connector comprises a snap-on adaptor ring 286. Snap-on adaptor ring 286 is sized to accommodate the cross-sectional shape of container 210. Snap-on adaptor ring 286 may be configured to loosely and frictionally engage container 210.

In another embodiment, the connector is a screw-on adaptor ring that releasably screws onto container 210. Inter-engaging threads on the inner surface of ring 286 engage threads on the outer surface of container 210. Threads may also engage threads on meter housing 231.

In another embodiment, the connector may be affixed to container 210 or housing 231 by, for example, welding, gluing, and the like. For instance, if the connector is permanently or semi-permanently affixed to container 210, then housing 231 may be releasably attached to the connector. For example, the releasable feature of connector 210 may be a quarter turn, snap fit, or thread. In another example, the connector may be permanently or semi-permanently affixed to meter housing 231 and releasably attached to container 210.

The shape of ring 286 may take a shape consistent with the cross-sectional shape of container 210 and meter housing 231. In one embodiment, the shape of ring 286 is a circle. In another embodiment, the shape of ring 286 is oval. In yet another embodiment, the shape of ring 286 is elliptical. In another embodiment, the shape of ring 286 is rectangular.

In yet another embodiment, the connector is sized to connect a container of a first cross-sectional shape and a meter housing of a second cross-sectional shape.

Figure 7C:
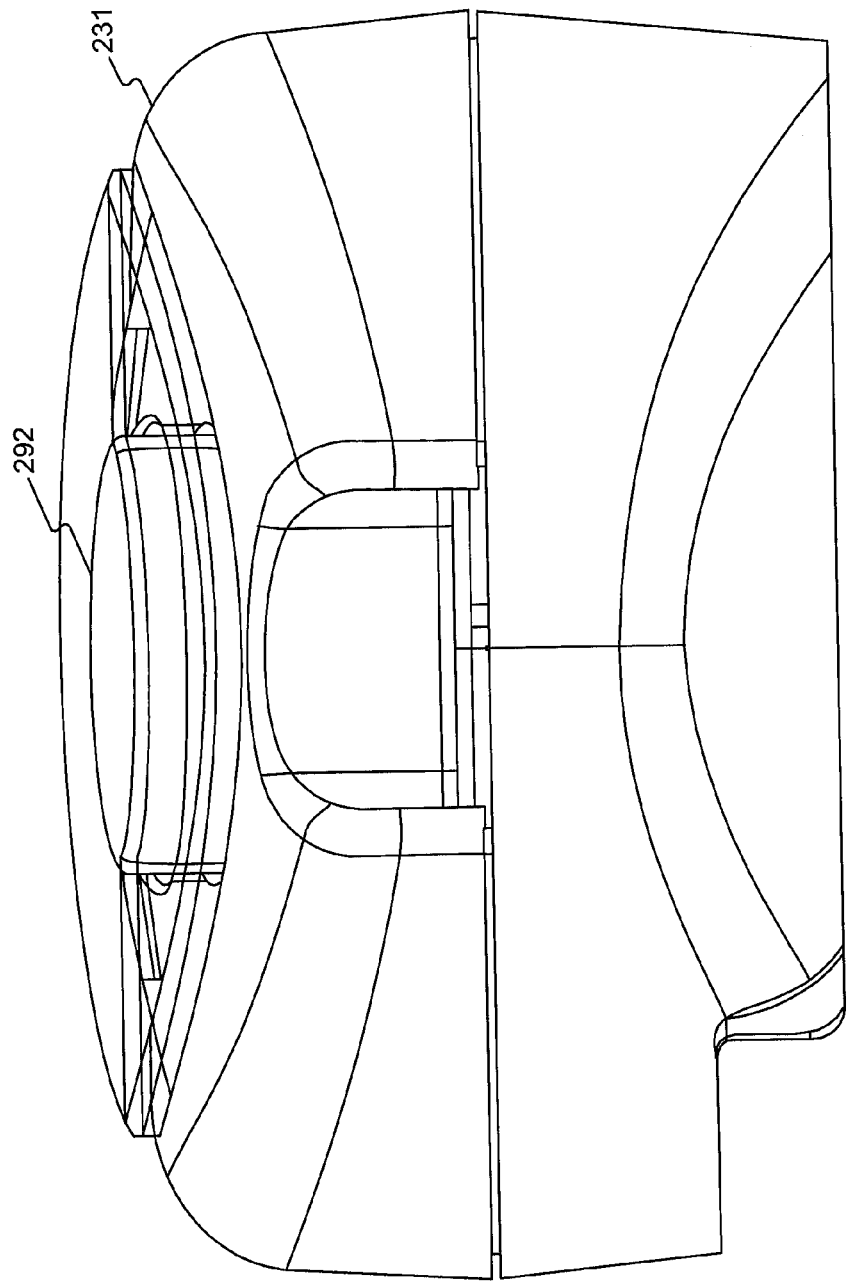
FIG. 7C is a view of the meter housing depicted in FIGS. 7A and 7B.

FIGS. 7A-7C depict an embodiment wherein housing 231 includes an eject button 292. Eject button 292 is configured, when depressed, to release housing 231 from container 210.

In FIGS. 7A-7C, eject button 292 is depicted as located on the upper portion of housing 231, yet the skilled artisan understands that eject button 292 may be located at any suitable position along housing 231.

Figure 8:
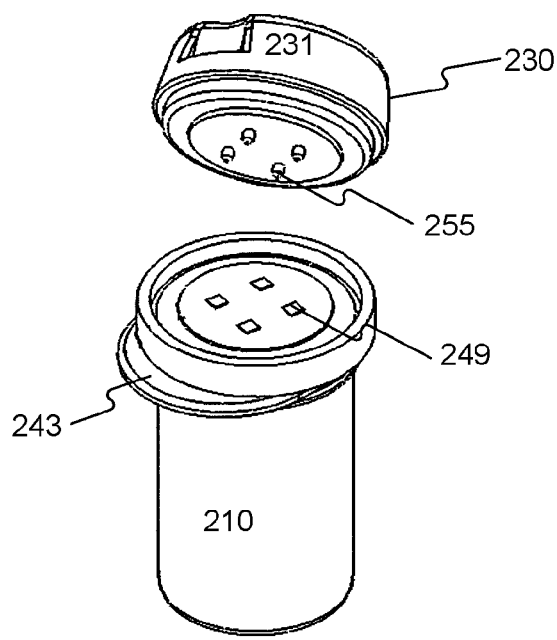
FIG. 8 is a perspective view of an embodiment of the system illustrating a meter having an interface for receiving a signal and a container having a coding element.

FIG. 8. is a perspective view of an embodiment of the system illustrating a meter having an interface for receiving a signal 255 and a container having a coding element 249. When removable meter 230 is attached to container 210, interface 255 makes contact with coding element 249 to receive a signal representing coding information.

In an exemplary embodiment, container 210 and closure 240 are formed of polypropylene using an injection molding process. However, other materials and processes may be used without departing from the scope of the present invention.

Other embodiments will be apparent to those skilled in the art from consideration of the specification and practice of the embodiments disclosed herein. It is intended that the specification and examples be considered as exemplary only.

What is claimed is:

1. A system for diagnostic testing comprising:
an electronic meter for performing a diagnostic test on a sample applied to test media, the electronic meter comprising a housing having a test media port and an interface for receiving a signal representing coding information;
a plurality of test media compatible with the electronic meter, each test media of the plurality of test media having a first end and a second end, the first end having a width and a height, wherein a width and a height of the test media port is approximately equal to the width and the height of the first end for insertion of the first end into the test media port; and
a container having an open interior volume permitting contact between the plurality of test media housed therein, the container having a coding element associated therewith and a top end;
wherein at least one of the housing and the container comprises a top mount attachment configured to releasably attach the housing to the container; and
the coding element associated with the container transmit the coding information to the interface when the housing is attached to the container.

2. The system according to claim 1, wherein the top mount attachment is configured to releasably mount the housing to the top end of the container.

3. The system according to claim 1, wherein the top mount attachment comprises at least one lock protruding from the housing and at least one corresponding protrusion protruding from at least a portion of a lip of the container, each lock configured to slidably traverse at least a portion of each protrusion, wherein in a first position, each lock and each protrusion are disengaged so that the housing is capable of being removed from the top end of the container, and wherein in a second position, each lock and each protrusion are engaged so that the housing is prevented from being removed from the top end of the container.

4. The system according to claim 3, wherein the housing is rotated about a central axis to transit from the first position to the second position.

5. The system according to claim 1, wherein the housing comprises at least one tab extending from a side wall of the housing, wherein the tab has a top surface.

6. The system according to claim 5, wherein the top surface of each tab comprises one or more ridges.

7. The system according to claim 5, wherein the tab extends at an angle from the side wall, wherein the angle, relative to a vertical plane substantially parallel to the side wall, ranges from about 1 degree to about 90 degrees.

8. A system for diagnostic testing comprising:
an electronic meter for performing a diagnostic test on a sample applied to test media, the electronic meter comprising a housing having a test media port and an interface for receiving a signal representing coding information;
a plurality of test media compatible with the electronic meter, each test media of the plurality of test media having a first end and a second end, the first end having a width and a height, wherein a width and a height of the test media port is approximately equal to the width and the height of the first end for insertion of the first end into the test media port;
a container configured to contain test media compatible with the electronic meter, the container having a coding element associated therewith and a top end;
wherein at least one of the housing and the container comprises a top mount attachment configured to releasably attach the housing to the container; and
the coding element associated with the container transmits the coding information to the interface when the housing is attached to the container;
wherein the top mount attachment comprises at least one lock protruding from the housing and at least one corresponding protrusion protruding from at least a portion of a lip of the container, each lock configured to slidably traverse at least a portion of each protrusion when the housing and the container are rotated with respect to one another;
wherein in a first rotation position, each lock and each protrusion are disengaged so that the housing is capable of being removed from the top end of the container; and
wherein in a second rotation position, each lock and each protrusion are engaged so that the housing is prevented from being removed from the top end of the container.

9. The system according to claim 1, wherein the test media port is positioned on an outer surface of the housing.

10. The system of claim 9, wherein, when a test media of the plurality of test media is inserted into the media port, the first end of the test media extends into the test media port and the second end of the test media extends away from the test media port and electronic meter.

11. The system according to claim 1 further comprising at least one top mount attachment configured to releasably engage the housing and the container, wherein the at least one top mount attachment is configured to releasably remove the container and releasably attach a second container.

12. The system according to claim 8, wherein the test media port is positioned on an outer surface of the housing.

13. The system of claim 12, wherein, when a test media of the plurality of test media is inserted into the media port, the first end of the test media extends into the test media port and the second end of the test media extends away from the test media port and electronic meter.

* * * * *